United States Patent [19]

Mahler et al.

[11] Patent Number: 4,793,329

[45] Date of Patent: Dec. 27, 1988

[54] SHOCK WAVE SOURCE

[75] Inventors: Matthias Mahler, Erlangen; Manfred Rattner, Buckenhof, both of Fed. Rep. of Germany

[73] Assignee: Siemens Aktiengesellschaft, Berlin and Munich, Fed. Rep. of Germany

[21] Appl. No.: 98,843

[22] Filed: Sep. 21, 1987

[30] Foreign Application Priority Data

Oct. 6, 1986 [DE] Fed. Rep. of Germany ... 8627238[U]

[51] Int. Cl.$^4$ .............................................. A61B 17/22

[52] U.S. Cl. ................................... 128/24 A; 367/175

[58] Field of Search ............. 128/24 A, 328; 367/182, 367/141, 142, 175, 163, 174; 181/402, 142

[56] References Cited

U.S. PATENT DOCUMENTS 4,674,505 6/1987 Pauli et al. .......................... 128/328

FOREIGN PATENT DOCUMENTS 1532008 11/1978 Canada .

3312014 10/1984 Fed. Rep. of Germany .

3502751 7/1986 Fed. Rep. of Germany ...... 128/328

3505894 8/1986 Fed. Rep. of Germany ...... 128/328

*Primary Examiner*—Ruth S. Smith

*Attorney, Agent, or Firm*—Hill, Van Santen, Steadman & Simpson

[57] ABSTRACT

A shock wave source of the type suitable for treating calculi in the body of a patient has a shock wave tube filled with a shock wave-conducting medium which is closed at one end by a flexible cover adapted to be pressed against the patient, and closed at an opposite end by a membrane. A flat coil is disposed parallel to and spaced from the membrane, with an insulation layer therebetween. The coil is connected to a high voltage pulse generator. The membrane consists of an insulator disc having electrically conductive tracks thereon, preferably concentrically disposed. The conductive tracks constitute a significantly lengthened path which must be overcome in order to generate an arc between the membrane and the coil, so that unwanted arcing is substantially eliminated.

3 Claims, 1 Drawing Sheet

SHOCK WAVE SOURCE

BACKGROUND OF THE INVENTION

1. Field of the Invention

The present invention is directed to a shock wave source of the type suitable for treating calculi in the body of a patient by disintegrating the calculi.

2. Description of the Prior Art

Shock wave sources are known for use in lithotripsy which include a liquid-filled shock wave tube having one end closed by a flexible cover which can be pressed against the patient by means of the fluid pressure of the liquid, and an opposite end which is closed by a membrane. The membrane is disposed opposite a flat coil with an insulating layer therebetween. The coil is connected to a high voltage pulse generator.

Shock wave sources of this type are used, for example, for disintegrating kidney stones. For this purpose, an acoustic lens is disposed in the shock wave tube, which focusses the shock wave generated by the flat coil and the membrane to a focus at which the kidney stone is disposed. The particles of the kidney stone disintegrated in this manner can then be eliminated naturally.

In known shock wave sources, the flat coil is formed by a helical winding, having one end which is grounded. The membrane disposed opposite the coil consists of electrically conductive material, and is also grounded. When a high voltage pulse is supplied to the flat coil, the membrane is magnetically repelled due to the eddy currents produced, and initially generates a planar shock wave in the fluid in the shock wave tube, which is focussed onto the calculus by the acoustic lens. The voltage between the coil at its high-voltage end and the membrane is the same as the maximum value available from the high-voltage source, so that arcing, which can destroy the membrane, may occur.

SUMMARY OF THE INVENTION

It is an object of the present invention to provide a shock wave source of the type described above wherein the risk of arcing between the flat coil and the membrane is substantially reduced in comparison to conventional shock wave sources.

The above object is achieved in accordance with the principles of the present invention in a shock wave source wherein the membrane consists of an insulator disc having electrically conductive tracks thereon. The membrane is thus not electrically conductive overall, but only has electrically conductive tracks which are separated from one another by insulation. The total path which then must be overcome for arcing to occur constitutes twice the length of the electrically conductive tracks from the flat coil, and additionally includes the distances between the individual conductive tracks. This arcing path is thus considerably lengthened in comparison to conventional shock wave sources, making arcing much less likely to occur.

A plurality of conductive tracks in the shock wave source disclosed herein have been used in favor of a single, conductive track, because the plurality of conductive tracks provide not only the advantage of lengthening the path which must be overcome for arcing to occur by virtue of the spacings between the individual conductive tracks but also provide the advantage of lower mass. Consequently, a lower energy is required to accelerate the membrane when a plurality of conductive tracks are used or, if the energy level is maintained the same, a greater acceleration of the membrane will be achieved, and thus a steeper pressure rise of the generated shock wave. An optimally steep pressure rise is desirable because the ability of the shock waves to disintegrate the calculi becomes greater as the pressure rise becomes steeper.

DESCRIPTION OF THE PREFERRED EMBODIMENTS

Figure 1:
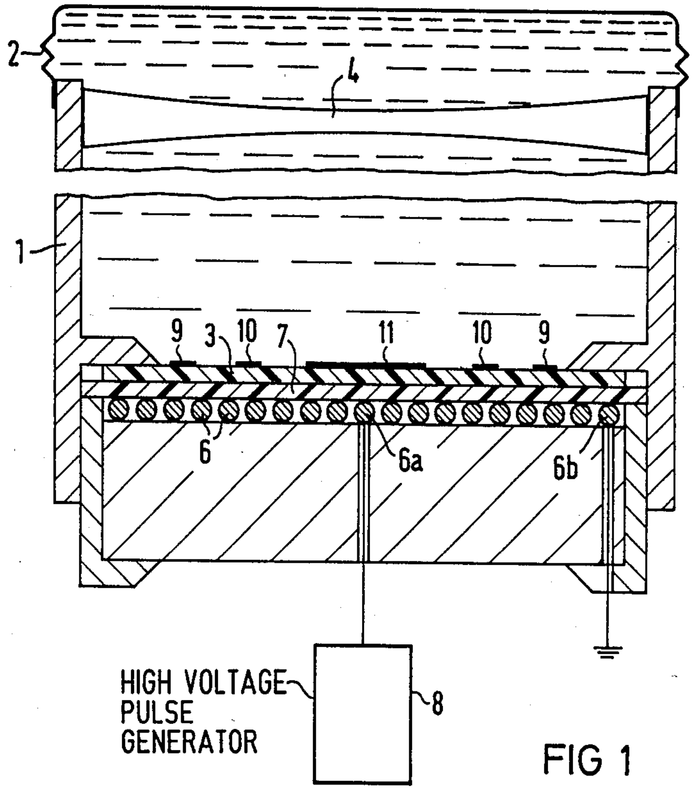
FIG. 1 is a side sectional view of a shock wave source constructed in accordance with the principles of the present invention.

A shock wave tube 1 is shown in FIG. 1, which is filled with water as a coupling agent, the pressure thereof being capable of being controlled in a known manner, which is not shown. The side of the shock wave tube 1 which is to be applied to a patient is closed with an elastic cover 2. The opposite end is closed by a membrane 3. A acoustic lens 4 for focussing the shock waves onto a focus in the body of the patient is disposed inside of the shock wave tube 1. An insulating layer 7 is disposed between the membrane 3 and a flat coil 6, which is helical. An end 6*a* of the flat coil 6 at the high-voltage side is connectable to a high-voltage pulse generator 8. The other end 6*b* of the flat coil 6 is grounded.

For generating shock waves, the flat coil 6 is supplied with high-voltage pulses of, for example, 20 kV. As a result, eddy currents are generated in the membrane 3 which cause the membrane 3 to be rapidly repelled from the flat coil 6. Planar shock waves are initially generated in the liquid (water) in the shock wave tube 1, which are focussed by the acoustic lens 4 in the desired manner.

Figure 2:
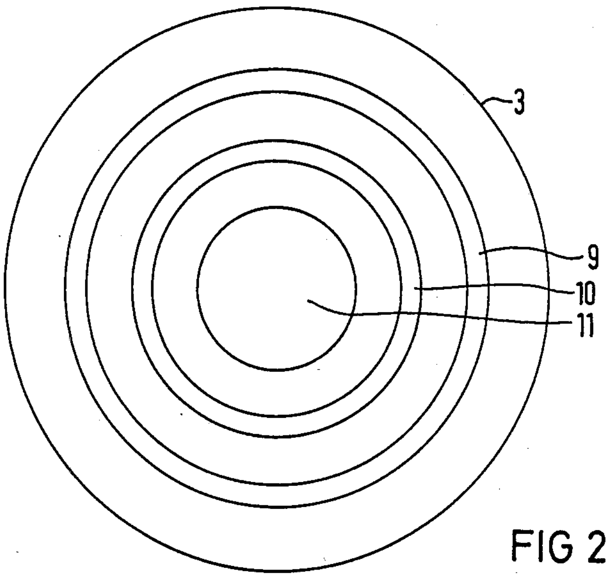
FIG. 2 is a plan view of the membrane used in the shock wave source of FIG. 1.

For reducing the risk of voltage arcing between the two coil ends 6*a* and 6*b* (which arcing would proceed through the membrane 3), the membrane 3 as shown in FIG. 2 consists of a circular insulator disc having a plurality of electrically conductive tracks 9, 10 and 11 thereon. These tracks are also shown exaggerated in the side view of FIG. 1. The tracks 9, 10 and 11 may consist, for example, of silver plated copper. The tracks 9 and 10 may be in the form of concentric rings, with the track 11, generally in the center of the membrane 3, being a disc of electrically conductive material.

As can be seen from FIG. 2, the path which would have to be overcome for arcing to occur between the two coil ends 6*a* and 6*b* is equal to twice the distance between the membrane 3 and the flat coil 6, plus the distances between the conduct tracks 9, 10 and 11. This path is so long that the possibility of arcing is virtually eliminated.

Although modifications and changes may be suggested by those skilled in the art it is the intention of the inventors to embody within the patent warranted hereon all changes and modifications as reasonably and properly come within the scope of their contribution to the art.

We claim as our invention:

1. A shock wave source for treating calculi disposed in the body of a patient, said shock wave source comprising:

a shock wave tube having a volume filled with a shock wave-conducting medium closed at one end by a flexible cover adapted for application against said patient and closed at an opposite end by a membrane consisting of electrically insulating material;

an insulating layer disposed adjacent said membrane;

means for generating a high voltage pulse;

a flat coil disposed adjacent said insulating layer connected to said means for generating a high-voltage pulse such that upon supply of a high-voltage pulse to said coil said membrane is rapidly repelled therefrom thereby generating a shock wave in said shock-wave conducting medium;

means for focussing said shock wave at said calculi; and a plurality of electrically conductive tracks disposed on said membrane, said tracks being spaced from each other on said membrane with said insulating material of said membrane therebetween to reduce arcing between said tracks and said coil.

2. A shock wave source as claimed in claim 1, wherein said conductive tracks on said membrane include a plurality of concentric rings.

3. A shock wave source as claimed in claim 2, wherein said conductive tracks on said membrane further include a disc of conductive material disposed substantially in a center of said membrane.

* * * * *